United States Patent [19]
Inaba et al.

[11] Patent Number: 4,552,751
[45] Date of Patent: Nov. 12, 1985

[54] LONG-LASTING MULTI-LAYERED FILM PREPARATION

[75] Inventors: Kohji Inaba, Neyagawa; Seiei Sasatani, Matsubara; Tatsushi Koide, Fujiidera; Tamio Nanya, Sakai, all of Japan

[73] Assignee: Ono Pharmaceutical Co., Ltd., Osaka, Japan

[21] Appl. No.: 312,458

[22] Filed: Oct. 19, 1981

[30] Foreign Application Priority Data

Oct. 17, 1980 [JP] Japan .................. 55-144503

[51] Int. Cl.⁴ .................. A01N 25/26; A01N 25/34
[52] U.S. Cl. .................. 424/19; 424/16; 424/21; 424/28; 514/443; 514/573
[58] Field of Search .................. 424/16, 19, 21, 28, 424/275, 317; 128/127, 260; 427/3; 604/890, 892, 896, 897

[56] References Cited

U.S. PATENT DOCUMENTS

| | | | |
|---|---|---|---|
| 3,926,188 | 12/1975 | Baker et al. | 128/260 |
| 4,180,558 | 12/1979 | Goldberg et al. | 424/28 |
| 4,265,874 | 4/1980 | Bonsen et al. | 424/16 |
| 4,317,447 | 3/1982 | Williams | 128/260 |
| 4,335,097 | 6/1982 | David et al. | 424/19 |
| 4,483,846 | 11/1984 | Koide et al. | 424/19 |

OTHER PUBLICATIONS

Derwent 35619 E/18.
Derwent 37166 D/21.
Derwent 43052 W/16.
Derwent 47633 V/26.
Chem. Abs. 93:191993d, (1980).
Remington's Pharmaceutical Science, 15th Ed.; 1975, Ch. 91, Mack Pub. Co., Easton, Pa.

*Primary Examiner*—Esther M. Kepplinger
*Assistant Examiner*—Shawn P. Foley
*Attorney, Agent, or Firm*—Sughrue, Mion, Zinn, Macpeak and Seas

[57] ABSTRACT

The present invention provides multi-layered film preparations which comprise one or more water soluble polymer bases, one or more water insoluble polymer bases, one or more plasticizers and one or more prostaglandins, and optionally contain one or more organic acids, and they are composed of at least two drug release controlling layers and one or more drug storing layers. The multi-layered film preparations of the present invention are characterized by that the prostaglandin(s) containing therein exhibit the desired long-lasting release patterns at the concentration required for therapeutic purpose.

16 Claims, 2 Drawing Figures

LAYER 1: DRUG RELEASE CONTROLLING LAYER
LAYER 2 AND LAYER 3: DRUG STORING LAYER

LAYER 1: DRUG RELEASE CONTROLLING LAYER
LAYER 2 AND LAYER 3: DRUG STORING LAYER

4: HPC FILM PREPARATION
5: HPTG FILM PREPARATION
6: FILM PREPARATION OF EXAMPLE 6
7: FILM PREPARATION OF EXAMPLE 1

LONG-LASTING MULTI-LAYERED FILM PREPARATION

BACKGROUND OF THE INVENTION

1. Field of the Invention

This invention relates to novel multi-layered film preparations and processes for the production thereof. More specifically, this invention relates to the multi-layered film preparations obtained by the combination of water soluble bases and water insoluble bases, characterized by that the prostaglandin or prostaglandins contained therein exhibit the desired long-lasting release patterns, further fully satisfying the purposes expected on prostaglandins aiming to lend themselves to uses as drug preparations which have high biological availability and are effective and safe, as well as the processes for the production thereof.

2. Description of the Prior Art

Various techniques for releasing drugs for an extended period of time have heretofore been reported in the literature. For instance, there are known coating methods to maintain release for an extended period of time as found mainly in oral tablets, intravaginally devices, drug release devices utilizing the osmotic pressure and despensers utilizing semipermeable membranes or porous membranes etc. In more recent years, there have also been reported the development of polymers for achieving long-lasting release intended for topical applications, long-lasting films and containers for releasing the drug quantitatively by release from one side; in any case, however, they have disadvantages that high levels of techniques and equipment are required and that the form of that device (preparation) is retained even in the vital body (administration site) to give an extraneous feel to the human. Further, they also have such disadvantages that the expected drug efficacy is difficult to obtain because the stability of the active ingredient is adversely affected, the biological availability is low and the like.

SUMMARY OF THE INVENTION

Accordingly, an object of this invention is to provide multi-layered film preparations which have eliminated the disadvantages of the conventional techniques, that is, which, when prostaglandins are administered at the mucosal site, e.g. intravaginally, release the drug at the desired concentration and can make this release long lasting and further have improved the stability of the prostaglandins contained therein and in which the shape of the preparation is not retained at the administered site after administration.

Another object of this invention is to provide multi-layered film preparation which control the long-lasting release by making the drug storing layers and the drug release controlling layers into the multi-layered form, and, therefor, which release the active ingredient at the concentration required for therapeutic purpose.

DETAILED DESCRIPTION OF THE INVENTION

The present invention provides multi-layered film preparation which comprise one or more water soluble polymer bases, one or more water insoluble polymer bases, one or more plasticizers and one or more prostaglandins, and optionally contain one or more organic acids, and they are composed of at least two drug release controlling layers and one or more drug storing layers.

The water soluble polymer bases included in this invention include biologically inactive, conventional water soluble polymers, preferably hydroxypropyl cellulose, polyvinylpyrrolidone, hydroxypropyl methyl cellulose etc., their average molecular weights preferably being 10,000–400,000.

The water insoluble polymer bases included in this invention include biologically inactive, conventional water insoluble polymers, preferably cellulose acetate, vinyl acetate resin etc., their average degrees of polymerization preferably being 100–500.

The plasticizers included in this invention include biologically inactive, conventional plasticizers, preferably diethyl phthalate, butyl phthalyl butyl glycolate, glycerin triacetin, tributyrin, polyethylene glycol, polypropylene glycol, propylene glycol, diethylene glycol, triethylene glycol, dipropylene glycol etc.

The prostaglandins included in this invention include prostaglandin F compounds, prostaglandin E compounds and 6,9-thio-prostaglandin $I_1$ compounds having uterine contractile activity and/or effect to enlarge the uterocervical canal, and preferably they are prostaglandin F, prostaglandin E and 6,9-thio-prostaglandin $I_1$ analogues effective for induction of menstruation, abortion or induction of labour by intravaginal administration.

The organic acids included in this invention include such organic acids as citric acid, tartaric acid, succinic acid, stearic acid, palmitic acid etc., preferably citric acid, tartaric acid.

The multi-layered film preparations (hereinafter referred to as the preparations of this invention) are preferably administered to the mucosal tissue in the vital body, particularly intravaginal administration is ideal.

Figure 1:
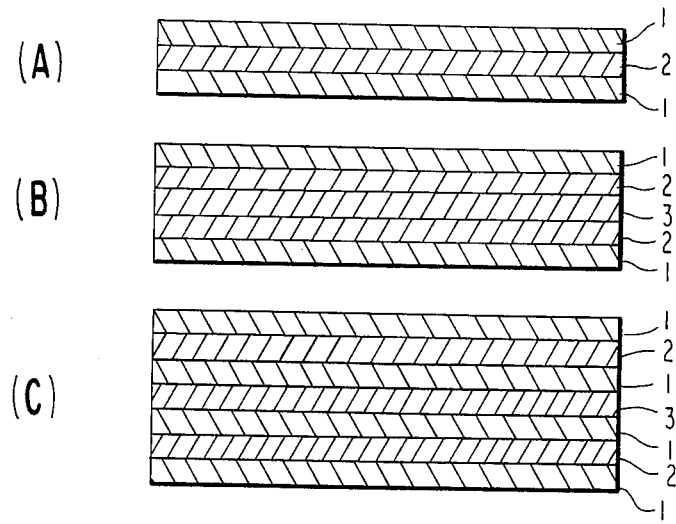
FIGS. 1(A), (B) and (C) are cross-sectional views showing an example of the multi-layered film preparations of this invention.

The important characteristics of the preparations of this invention are more fully described by setting forth some examples as shown in FIG. 1(A), (B) and (C) (which are intended to give more understanding thereof but not to limit this invention to these examples).

The preparations of this invention comprises at least two drug release controlling layers (Layer 1 in FIG. 1) and one or more drug storing layers (Layer 2 and Layer 3 in FIG. 1), and the two upper and lower layers on the outside are the drug release controlling layers. The size is preferably such that the surface area (the sum of the surface areas of the two upper and lower surfaces) is 1.5–30 cm$^2$ and the thickness is 0.1–3 mm, especially the size of 4–15 cm$^2$ in surface area and 0.2–2 mm in thickness being desired.

The drug release controlling layers comprises (A) one or more water soluble polymer compounds, (B) one or more water insoluble polymer compounds and (C) one or more plasticizers, and on administration to the mucosal tissue in the vital body, they are swollen and dissolved or decomposed with the body liquid. By this, the body liquid permeates into the drug storing layer or layers, and the drug contained therein is leached out.

The drug release is controlled by the physical properties that the drug release controlling layers are dissolved or decomposed with the body liquid.

In order to obtain the release rate of the drug and the long-lasting properties of the release suitable for the kind and properties of the drug contained in the preparations of this invention, and for the expected drug efficacy etc., this is effected by (i) meeting the purposes by changing the constitutional ratio of the water soluble polymer compounds to water insoluble polymer compounds constituting the drug release controlling layers thereby properly establishing the physical properties of being dissolved or decomposed with the body liquid, and/or by (ii) meeting the purposes by properly establishing the ratio of the surface area to thickness of the drug release controlling layers and/or by (iii) meeting the purposes by properly establishing the number of the drug release controlling layers [for example, FIG. 1(C)]. In the case of (iii), the thicknesses of the respective layers may be the same or different. In addition, the kinds and the constitutional ratios of the polymer compounds constituting the respective layers may be the same or different.

While the drug release controlling layers most often do not contain any drug, it is possible to incorporate a minor amount of the drug in the drug release controlling layers where it is necessary to release the drug in the earlier stage after administration.

The drug storing layers comprise one or more water soluble polymer compounds, or one or more of each of (A) water soluble polymer compounds and (B) plasticizers, or one or more of each of (A) water soluble polymer compounds, (B) water insoluble polymer compounds and (C) plasticizers, and contain required amounts of the drug.

The release rate of the drug and the long-lasting properties of the release suitable for the kind and properties of the drug contained in the drug storing layers and for the expected drug efficacy etc. may also be achieved by making the drug storing layers in the following manner:

(i) using a water soluble polymer compound or compounds and water insoluble polymer compound or compounds, and properly establishing the constitutional ratio thereof, and/or (ii) making two or more drug storing layers having different kinds and constitutional ratios of the constituting polymer compounds [for example, FIG. 1(B) or (C)], and/or (iii) making two or more drug storing layers having different levels of the drug [for example, FIG. 1(B) or (C)], and/or (iv) properly establishing the thickness of each drug storing layer.

Further, in this invention, it is also possible to contain two or more drugs having different pharmacological properties in separate drug storing layers to provide medicines ideal from an aspect of the drug efficacy. For example, for the purpose of induction of labour or abortion, five-layered or seven-layered film preparations which contain a prostaglandin having a strong effect to enlarge the uterocervical canal such as 16,16-dimethyl-trans-$\Delta^2$-PGE$_1$ methyl ester (hereinafter simply referred to as ONO-802) in the drug storing layer 2 in (B) or (C) of FIG. 1 and a prostaglandin having a strong uterine contractile effect such as 16,16-dimethyl-6,9-thio-PGI$_1$ methyl ester in the drug storing layer 3 enlarge the uterocervical canal and thereafter bring about contraction of the uterus, and therefore ideal.

In the drug release controlling layers or the drug storing layers, when the water soluble polymer compound(s) and the water insoluble polymer compound(s) are employed in combination, the constitutional ratio (by weight) thereof may be freely established in the range of 1–9 of the water soluble polymer compound(s) to 9–1 of the water insoluble polymer compound(s), and particularly preferred is 5–9 of the former to 5–1 of the latter.

The water soluble polymer compounds are commercially available in several specifications classified depending on the molecular weight of the polymer contained, and by using a different specification or by employing two or more of these specifications in combination, a more advantageous preparation meeting the purposes may be obtained. Preferably, the water soluble polymer compound is contained at a proportion of 10–80% in the preparation of the present invention.

Also with the water insoluble polymer compounds, there are several products of different specifications on the market, a similar effect may be achieved by using a different specification or by employing two or more of these in combination. Preferably, the water insoluble polymer compound is contained at a proportion of 10–80% in the preparation of the present invention.

Further, in this invention, since it is possible to make a soft, flexible film preparation suitable for the administration site by changing the kinds of the plasticizers to be used or by employing two or more plasticizers in combination, the disadvantages with the conventional film preparations can be eliminated, a physical difficulty in the administration site may be prevented and an effect to enhance the release properties of the active ingredient is obtained. Preferably, the plasticizer is contained at a proportion of 10–30% in the preparation of the present invention.

Still further in this invention, although stability of prostaglandin(s) can be adequately maintained even without incorporating an organic acid in the preparations sufficiently to provide products, addition of an organic acid gives more stable prostaglandin preparations. Though the organic acid to be added is not particularly restricted, citric acid, tartaric acid, succinic acid etc. are effective, and among these citric acid or tartaric acid is especially preferred. The amount of the organic acid to be added is preferable such that it is added to the preparation at a proportion of 0.01–0.5%, particularly preferably 0.05–0.3%.

The features of the preparations obtained according to this invention are as follows:

(1) By combining properly the drug storing layers and the drug release controlling layers, the release of the drug may be controlled according to the desired purpose to render it long-lasting.
(2) They may be applied to the site where the active ingredient are absorbed through the mucous membrane.
(3) Since the form of the film can be fully dissolved or decomposed with the body liquid, the physical difficulty may be prevented thus giving no extraneous feeling.
(4) During the film formation step, by addition of an organic acid, even unstable materials are hardly decomposed, and therefore stability can be retained for an extended period of time.
(5) Since a constant release pattern of the drug is obtained regardless of the individuals, high effectiveness is exhibited at a low dosage level of the drug.

(6) Since the biological availability is high and hence a dosage level of the drug may be low, there is no possibility for overdose and therefore safer preparations may be presented.

The process for the production of the preparations of this invention may be exemplified by a method which comprises preparing a drug release controlling layer solution (a solution for preparing drug release controlling layers) and a drug storing layer solution (a solution for preparing drug storing layers) respectively, and thereafter either (1) removing the organic solvents of the respective solutions by drying to prepare film-formed layers respectively, and mounting them, one on another, by a dry laminate or wet laminate method to prepare the desired multi-layered film preparation or (2) coating the drug storing layer solution on a film obtained by removing the organic solvent of the drug release controlling layer solution by drying, then removing the organic solvent by drying, and repeating these operations to prepare respective film-formed layers successively, thereby preparing the desired multi-layered film preparation.

The drug release controlling layer solution may be obtained by dissolving one or more water insoluble polymer compounds and one or more plasticizers in an organic solvent and, when a transparent solution is formed, adding one or more water soluble polymer compounds thereto and dissolving it over an adequate period of time, and if desired, adding a prostaglandin solution containing or not containing an organic acid dissolved in an organic solvent and further allowing it to stand and adequately deaerating it.

The drug storing layer solution may be obtained, (i) by dissolving one or more water soluble polymer compounds or a mixture of one or more water soluble polymer compounds and one or more water insoluble polymer compounds in an organic solvent and, when a transparent solution is formed, adding one or more plasticizers according to the desirability, and adding a prostaglandin solution containing or not containing an organic acid dissolved in an organic solvent, stirring uniformly, allowing it to stand and adequately deaerating it, (ii) by dissolving one or more water insoluble polymer compounds and one or more plasticizers in an organic solvent and, when a transparent solution is formed, adding one or more water soluble polymer compounds thereto and dissolving it over an adequate period of time, and adding a prostaglandin solution containing or not containing an organic acid dissolved in an organic solvent, stirring uniformly and further allowing it to stand and adequately deaerating it, or (iii) by dissolving one or more water soluble polymer compounds and one or more plasticizers in an organic solvent and, when a transparent solution is formed, adding a prostaglandin solution containing or not containing an organic acid dissolved in an organic solvent, stirring uniformly and allowing it to stand and adequately deaerating it.

While the organic solvent to be used may be any as long as it can dissolve the respective components for the preparation and is inert to them, methanol, ethanol, acetone, methylene chloride etc. are preferred, and they may be used either alone or in combination.

As the drying method, a conventional method such as standing at room temperature, drying with moderate heating, fluidized bed drying etc. can be used, but from the viewpoint of stability of prostaglandins drying at elevated temperatures is not proper. A temperature of between room temperature and 60° C. is preferred. Therefore, it is preferred to dry using a device which can control the temperature and the air flow.

The size, shape, thickness etc. of the multi-layered film preparation may be properly established depending on the pharmacological properties of the prostaglandin contained therein, the purpose for use etc., and may be prepared using a conventional process for producing multi-layered film preparations.

This invention is more fully described by the following examples and experiment examples but this invention should in no way be restricted thereto.

EXAMPLE 1

(1) Preparation of a drug release controlling layer solution: 1.2 g of vinyl acetate resin, 200 mg of glycerin and 200 mg of triacetin were added to 40 ml of methanol and then stirred until transparent. Thereafter, 2.4 g of hydroxypropyl cellulose was added, and the solution was stirred and allowed to stand for effecting deaeration.

(2) Preparation of a drug storing layer solution: 1.88 g of hydroxypropyl cellulose, 10 mg of glycerin and 100 mg of triacetin were added to 20 ml of methanol and stirred. To the resulting solution was added a solution of 10 mg of ONO-802 and 3 mg of tartaric anhydride in 10 ml of methanol, and the solution was stirred and then allowed to stand for effecting deaeration.

(3) Production of multi-layered film preparations: (A) 10 ml of the drug release controlling layer solution was dried at room temperature by a casting method, and then 15 ml of the drug storing layer solution was poured and similarly dried. Finally, 10 ml of the drug release controlling layer solution was poured and similarly dried to obtain a three-layered film preparation of about 0.9 mm in thickness. (B) 10 ml portions of the drug release controlling layer solution were dried at room temperature using a casting method to obtain two films. The thus obtained two films were laminated with a film, obtained by similarly drying 15 ml of the drug storing layer solution, placed therebetween to obtain a three-layered film preparation of about 0.9 mm in thickness.

EXAMPLE 2

A three-layered film preparation of about 0.9 mm in thickness was obtained similarly as in Example 1, except that the vinyl acetate resin employed in Example 1 was replaced by cellulose acetate, the hydroxypropyl cellulose by hydroxypropyl methyl cellulose and the glycerin by butyl phthalyl butyl glycolate.

EXAMPLE 3

A three-layered film preparation of about 0.9 mm in thickness was obtained similarly as in Example 1, except that the hdryoxypropyl cellulose employed in Example 1 was replaced by polyvinylpyrrolidone.

EXAMPLE 4

(1) Using 130 mg of vinyl acetate resin, 70 mg of glycerin, 70 mg of triacetin, 20 ml of methanol and 1.07 g of hydroxypropyl cellulose, similar procedures as in (1) and (3) (B) of Example 1 were repated to obtain two films.

(2) 70 mg of vinyl acetate resin, 30 mg of glycerin and 30 mg of triacetin were added to 15 ml of methanol and stirred until transparent, after which 538.5 mg of hydroxypropyl cellulose was added and stirred. To this solution was added a solution of 1.5 mg of 16,16-dimethyl-6,9-thio-PGI$_1$ methyl ester dissolved in 5 ml of methanol, and the solution was stirred and allowed to stand for effecting deaeration. The resulting solution was dried at room temperature by a casting method to obtain a film.

(3) Using 1.26 g of hydroxypropyl cellulose, 65 mg of triacetin, 65 mg of glycerin, 15 ml of methanol, 2.5 mg of ONO-802, 2 mg of tartaric anhydride and 5 ml of methanol, similar procedures as in (2) and (3) (B) of Example 1 were repeated to obtain two films.

(4) Using a laminating method, the film obtained in (1), the film obtained in (3) the film obtained in (2), the film obtained in (3) and the film obtained in (1) were laminated successively to obtain a five-layered film preparation of about 1.0 mm in thickness.

EXAMPLE 5

A five-layered film preparation of about 1.0 mm in thickness was obtained similarly as in Example 4, except that the hydroxypropyl cellulose employed in Example 4 was replaced by polyvinylpyrrolidone.

EXAMPLE 6

(1) Using 300 mg of vinyl acetate resin, 150 mg of glycerin, 150 mg of triacetin, 30 ml of methanol and 2.4 g of hydroxypropyl cellulose, similar procedures as in (1) of Example 1 were repeated to obtain about 30 ml of the solution.

(2) A solution of 5 mg of ONO-802 and 1.5 mg of tartaric anhydride dissolved in one ml of methanol was added to 10 ml of the solution obtained in (1), stirred and then allowed to stand for effecting deaeration.

(3) Using 20 ml of the solution obtained in (1) and the solution obtained in (2), procedures similar as in (3) (B) of Example 1 were repeated to obtain a three-layered film preparation of about 0.9 mm in thickness.

Experiment Example 1

Figure 2:
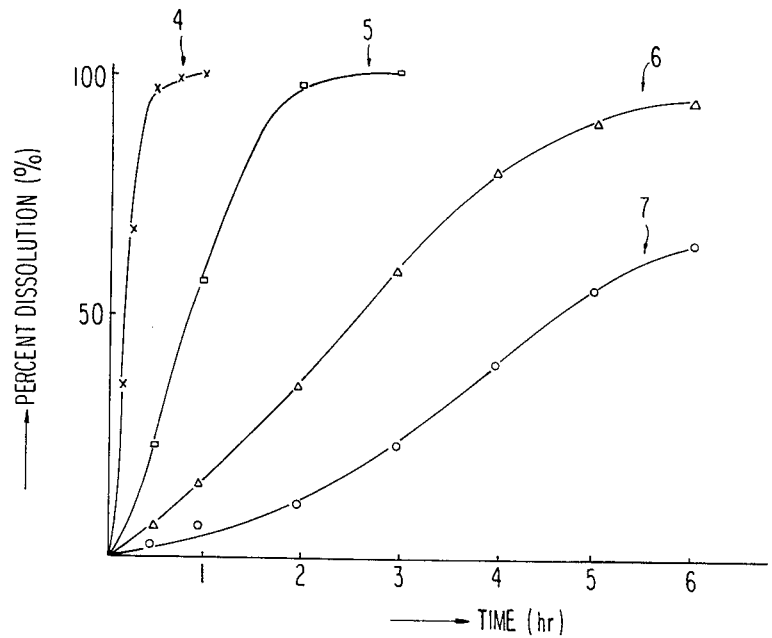
FIG. 2 is a graph showing the percent dissolution of the drug in various preparations.

In order to compare the following preparations: the multi-layered film preparations produced in Examples 1 and 6; a single-layered film preparation employing a water soluble polymer compound (prepared as described hereafter; and simply referred to as HPC film); and a single-layered film preparation employing a water soluble polymer compound and a water insoluble polymer compound (prepared as described hereafter; and simply referred to as HPTG film), for the release rate of the drug and the long-lasting properties of the release, a dissolution test was conducted according to the USP paddle method. The results of the experiment are shown in Table 1 and FIG. 2.

Preparation of HPC Film

A solution of 199.5 mg of hydroxypropyl cellulose in 2 ml of ethanol was stirred until a transparent solution was formed. The above cellulose solution was added to a solution of 0.2 mg of ONO-802 and 0.3 mg of tartaric anhydride in 1 ml of ethanol and the mixture was stirred uniformly. The solution thus obtained was dried at low temperature by a casting method to obtain HPC film.

Preparation of HPTG Film

A solution of 20 mg of vinyl acetate resin, 10 mg of glycerin and 10 mg of triacetin in 2 ml of methanol was stirred until a trasparent solution was formed. 30 mg of HPC-M (a registered Trade Mark; and a kind of hydroxypropyl cellulose) and 130 mg of HPC-L (a registered Trade Mark; and a kind of hydroxypropyl cellulose) were added thereto and the solution was stirred uniformly. To the solution thus obtained was added a solution of 0.2 mg of ONO-802 and 0.3 mg of tartaric anhydride in 1 ml of methanol and the solution was stirred uniformly. The solution thus obtained was dried at room temperature by a casting method to obtain HPTG film.

TABLE 1

| Sample | Percent Dissolution (%) in Various Preparations | | | | | | |
|---|---|---|---|---|---|---|---|
| | Dissolution Time (hr) | | | | | | |
| | 0.5 | 1 | 2 | 3 | 4 | 5 | 6 |
| HPC Film | 97.6 | 100 | | | | | |
| HPTG Film | 23.1 | 57.0 | 98.3 | 100 | | | |
| Film of Example 6 | 7.0 | 15.9 | 35.8 | 59.6 | 80.0 | 90.0 | 95.0 |
| Film of Example 1 | 2.9 | 6.4 | 11.2 | 23.3 | 39.6 | 55.6 | 65.2 |

Experiment Example 2

The multi-layered film preparation produced in Example 1 and HPTG film were compared for the uterine contractile activity which is the pharmacological activity of ONO-802 in non-anesthetized rats. In this test, each preparation cut into a size corresponding to the indicated dosage was administered. The results of the experiment are shown in Table 2.

TABLE 2

Comparison of Uterine Contractile Activity in Various Preparations (Intravaginal Administration to Non-anesthetized Rats)

| Dosage of ONO-802 ($\mu$g/kg) | Film of Example 1 | | HPTG Film | |
|---|---|---|---|---|
| | Effective Ex./ Total Ex. | Duration (min.) | Effective Ex./ Total Ex. | Duration (min.) |
| 200 | 8/8 | 600–720 | 8/8 | 400–450 |
| 400 | 8/8 | 720–780 | 8/8 | 450–500 |
| 800 | 8/8 | 840–900 | 6/6 | 470–540 |

The duration of the uterine contractile activity was greatly prolonged with the preparation of Example 1. The intensity of the activity of HPTG film is greater than that of the preparation of Example 1 at the same dose. About 400 $\mu$g dosage of the preparation of Example 1 corresponded to the 100 $\mu$g dosage of HPTG film. In the case of the dosage levels of the preparation of Example 1, a weak pattern was exhibited at 200 $\mu$g, while medium-level lasting pattern were exhibited both at 400 and 800 $\mu$g.

We claim:

1. A multi-layered pharmaceutical film preparation of 3, 5 or 7 layers comprising:
    (i) one or more drug storing layer(s) comprising components (A), (C) and (D) as defined below; and
    (ii) two or more drug release controlling layers consisting essentially of components (A), (B) and (C) as defined below:
        (A) one or more biologically inactive water soluble polymer compounds with an average molecular weight of 10,000–400,000 in an amount of from 10 to 80% by weight of the preparation, wherein said water soluble polymer compounds are selected from the group consisting of hydroxypropyl cellulose, polyvinylpyrrolidone and hydroxypropyl methyl cellulose;

(B) one or more biologically inactive water insoluble polymer compounds with an average degree of polymerization of 100–500, wherein said water insoluble polymer compounds are selected from the group consisting of cellulose acetate and vinyl acetate resin;

(C) one or more biologically inactive plasticizers, wherein said plasticizers are selected from the group consisting of diethyl phthalate, butyl phthalyl butyl glycolate, glycerin, triacetin, tributyrin, polyethylene glycol, polypropylene glycol, propylene glycol, diethylene glycol, triethylene glycol and dipropylene glycol and;

(D) one or more prostaglandins selected from the group consisting of prostaglandin F compounds, prostaglandin E compounds, and 6, 9 thio-prostaglandin $I_1$ compounds; wherein said drug release controlling layers are disposed on opposite sides of said drug storing layer(s) and wherein said drug storing layer(s) and drug release controlling layers are formulated so as to dissolve or decompose totally after administration to a mucosal site.

2. A multi-layered pharmaceutical film preparation according to claim 1 which has a surface area of 1.5–30 $cm^2$ and a thickness of 0.1–3 mm.

3. A multi-layered pharmaceutical film preparation according to claim 1 in which the water insoluble polymer compound is contained at a proportion of 10–80% by weight of the preparation.

4. A multi-layered pharmaceutical film preparation according to claim 1 in which the plasticizer is contained at a proportion of 10–30% by weight of the preparation.

5. A multi-layered pharmaceutical film preparation of 3, 5 or 7 layers comprising:

(i) one or more drug storing layer(s) comprising components (A), (C) and (D) as defined below, and additionally either alone or in combination, components (B) or (E) as defined below; and (ii) two or more drug release controlling layers consisting essentially of components (A), (B) and (C) as defined below:

(A) one or more biologically inactive water soluble polymer compounds with an average molecular weight of 10,000–400,000 in an amount of from 10 to 80% by weight of the preparation, wherein said water soluble polymer compounds are selected from the group consisting of hydroxypropyl cellulose, polyvinylpyrrolidone and hydroxypropyl methyl cellulose;

(B) one or more biologically inactive water insoluble polymer compounds with an average degree of polymerization of 100–500, wherein said water insoluble polymer compounds are selected from the group consisting of cellulose acetate and vinyl acetate resin;

(C) one or more biologically inactive plasticizers, wherein said plasticizers are selected from the group consisting of diethyl phthalate, butyl phthalyl butyl glucolate, glycerin, triacetin, tributyrin, polyethylene glycol, polypropylene glycol, propylene glycol, diethylene glycol, triethylene glycol and dipropylene glycol;

(D) one or more prostaglandins selected from the group consisting of prostaglandin F compounds, prostaglandin E compounds, and 6, 9 thio-prostaglandin $I_1$ compounds; and (E) one or more organic acids wherein said organic acid is selected from the group consisting of citric acid and tartaric acid, wherein said drug release controlling layers are disposed on opposite sides of said drug storing layer(s) and wherein said drug storing layer(s) and drug release controlling layers are formulated so as to dissolve or decompose totally after administration to a mucosal site.

6. A multi-layered pharmaceutical film preparation according to claim 5 which has a drug storing layer or layers comprising (A) one or more water soluble polymer compounds, (B) one or more water insoluble polymer compounds, (C) one or more plasticizers and (D) one or more prostaglandins.

7. A multi-layered pharmaceutical film preparation according to claim 5 in which the organic acid is contained at a proportion of 0.01–0.5% by weight of the preparation.

8. A three-layered pharmaceutical film preparation according to claim 5 which has two drug release controlling layers consisting essentially of vinyl acetate resin, glycerin, triacetin and hydroxypropyl cellulose, and therebetween one drug storing layer comprising hydroxypropyl cellulose, glycerin, triacetin, 16,16-dimethyl-trans-$\Delta^2$-$PGE_1$ methyl ester and tartaric acid.

9. A three-layered pharmaceutical film preparation according to claim 5 which has two drug release controlling layers consisting essentially of cellulose acetate, butyl phthalyl butyl glycolate, triacetin and hydroxypropyl methyl cellulose, and therebetween one drug storing layer comprising hydroxypropyl methyl cellulose, butyl phthalyl butyl glycolate, triacetin, 16,16-dimethyl-trans-$\Delta^2$-$PGE_1$ methyl ester and tartaric acid.

10. A three-layered pharmaceutical film preparation according to claim 5 which has two drug release controlling layers consisting essentially of vinyl acetate resin, glycerin, triacetin and polyvinylpyrrolidone, and therebetween one drug storing layer comprising polyvinylpyrrolidone, glycerin, triacetin, 16,16-dimethyl-trans-$\Delta^2$-$PGE_1$ methyl ester and tartaric acid.

11. A five-layered pharmaceutical film preparation according to claim 5 which has the structure mounting successively (1) a drug release controlling layer consisting essentially of vinyl acetate resin, glycerin, triacetin and hydroxypropyl cellulose, (2) a drug storing layer comprising hydroxypropyl cellulose, glycerin, triacetin, 16,16-dimethyl-trans-$\Delta^2$-$PGE_1$ methyl ester and tartaric acid, (3) a drug storing layer comprising vinyl acetate resin, glycerin, triacetin, hydroxypropyl cellulose and 16,16-dimethyl-6,9-thio-$PGI_1$ methyl ester, (4) the drug storing layer as mentioned in (2), and (5) the drug release controlling layer as mentioned in (1).

12. A five-layered pharmaceutical film preparation according to claim 5 which has the structure mounting successively (1) a drug release controlling layer consisting essentially of vinyl acetate resin, glycerin, triacetin and polyvinylpyrrolidone, (2) a drug storing layer comprising polyvinylpyrrolidone, glycerin, triacetin, 16,16-dimethyl-trans-$\Delta^2$-$PGE_1$ methyl ester and tartaric acid, (3) a drug storing layer comprising vinyl acetate resin, glycerin, triacetin, polyvinylpyrrolidone and 16,16-dimethyl-6,9-thio-$PGI_1$ methyl ester, (4) the drug storing layer as mentioned in (2), and (5) the drug release controlling layer as mentioned in (1).

13. A three-layered pharmaceutical film preparation according to claim 5 which has two drug release controlling layers consisting essentially of vinyl acetate resin, glycerin, triacetin and hydroxypropyl cellulose, and therebetween one drug storing layer comprising vinyl acetate resin, glycerin, triacetin, hydroxypropyl cellulose, 16,16-dimethyl-trans-$\Delta^2$-PGE$_1$ methyl ester and tartaric acid.

14. A multi-layered pharmaceutical film preparation according to claim 5 which has a surface area of 1.5–30 cm$^2$ and a thickness of 0.1–3 mm.

15. A multi-layered pharmaceutical film preparation according to claim 5 in which the water insoluble polymer compound is contained at a proportion of 10–80% by weight of the preparation.

16. A multi-layered film preparation according to claim 5 in which the plasticizer is contained at a proportion of 10–30% by weight of the preparation.

* * * * *